US009664761B2

(12) United States Patent
Liu

(10) Patent No.: US 9,664,761 B2
(45) Date of Patent: May 30, 2017

(54) JOINT ESTIMATION OF CHEMICAL SHIFT AND QUANTITATIVE SUSCEPTIBILITY MAP USING MRI SIGNAL

(71) Applicant: MedImageMetric LLC, New York, NY (US)

(72) Inventor: Tian Liu, New York, NY (US)

(73) Assignee: MedImageMetric LLC, New York, NY (US)

( * ) Notice: Subject to any disclaimer, the term of this patent is extended or adjusted under 35 U.S.C. 154(b) by 507 days.

(21) Appl. No.: 14/316,557

(22) Filed: Jun. 26, 2014

(65) Prior Publication Data
US 2015/0002148 A1 Jan. 1, 2015

Related U.S. Application Data

(60) Provisional application No. 61/839,625, filed on Jun. 26, 2013.

(51) Int. Cl.
| | |
|---|---|
| *G01V 3/00* | (2006.01) |
| *G01R 33/48* | (2006.01) |
| *A61B 5/055* | (2006.01) |
| *G01R 33/24* | (2006.01) |
| *A61B 5/00* | (2006.01) |
| *G01R 33/485* | (2006.01) |
| *G01R 33/565* | (2006.01) |

(52) U.S. Cl.
CPC .......... *G01R 33/4828* (2013.01); *A61B 5/055* (2013.01); *G01R 33/243* (2013.01); *A61B 5/4872* (2013.01); *G01R 33/485* (2013.01); *G01R 33/56536* (2013.01)

(58) Field of Classification Search
CPC ................................................ G01R 33/56536
USPC .................................................. 324/307, 309
See application file for complete search history.

(56) References Cited

U.S. PATENT DOCUMENTS

| | | | |
|---|---|---|---|
| 9,097,779 B2* | 8/2015 | Fautz ................. | G01R 33/5605 |
| 2003/0212322 A1* | 11/2003 | Haacke .............. | A61B 5/02007 |
| | | | 600/410 |

(Continued)

OTHER PUBLICATIONS de Rochefort, et al., *Quantitative MR susceptibility mapping using piece-wise constant regularized inversion of the magnetic field.* Magn Reson Med 60(4):1003-1009 (Oct. 2008).

(Continued)

*Primary Examiner* — Louis Arana
(74) *Attorney, Agent, or Firm* — Fish & Richardson P.C.

(57) ABSTRACT

An example implementation of a method for mapping tissue magnetic susceptibility includes acquiring magnetic resonance (MR) images acquired at multiple echo times, where the MR images correspond to a subject comprising at least two species of protons, and where each species has a different chemical shift in its respective resonance frequency. The method also includes determining, for each species, an estimated chemical shift value, determining an estimated map of magnetic field inhomogeneity based on the estimated chemical shift values, determining an estimated susceptibility distribution of the subject and an error of each estimated chemical shift value based on the estimated map of magnetic field inhomogeneity and prior information regarding the subject, and generating an image of the subject based on the estimated susceptibility distribution.

20 Claims, 9 Drawing Sheets

(56) References Cited

U.S. PATENT DOCUMENTS

2015/0204955 A1* 7/2015 Gumbrecht ........ G01R 33/4828
324/322
2016/0313421 A1* 10/2016 Fuderer .............. G01R 33/4816

OTHER PUBLICATIONS de Rochefort, et al., *Quantitative susceptibility map reconstruction from MR phase data using bayesian regularization: validation and application to brain imaging*. Magn Reson Med 63(1):194206 (Jan. 2010).

Hernando, et al., *Robust water/fat separation in the presence of large field inhomogeneities using a graph cut algorithm*. Magn Reson Med 63(1):79-90 (Jan. 2010).

Liu, et al., *Calculation of susceptibility through multiple orientation sampling (COSMOS): a method for conditioning the inverse problem from measured magnetic field map to susceptibility source image in MRI*. Magn Reson Med 61(1):196-204 (Jan 2009).

Liu, et al., *Morphology enabled dipole inversion (MEDI) from a single-angle acquisition: comparison with Cosmos in human brain imaging*, Magn Reson Med 66(3):777-783 (Sep. 2011).

Liu, T., et al., *A novel background field removal method for MRI using projection onto dipole fields (PDF)*. NMR Biomed 24, 1129-1136 (Nov. 2011).

Liu, et al., *Morphology enabled dipole inversion for quantitative susceptibility mapping using structural consistency between the magnitude image and the susceptibility map*. NeuroImage 59(3):2560-2568 (Feb. 2012).

Liu, et al., *Nonlinear formulation of the magnetic field to source relationship for robust quantitative susceptibility mapping*. Magn Reson Med 69(2):467-476 (Feb. 2013).

Reeder, et al., *Multicoil Dixon chemical species separation with an iterative least-squares estimation method*, Magn Reson Med 51(1):35-45 (Jan. 2004).

Reeder, et al., *Iterative decomposition of water and fat with echo 25 asymmetry and least-squares estimation (IDEAL): application with fast spin-echo imaging*. Magn Reson Med 54(3):636-644 (Sep. 2005).

Reeder, et al., *Water-fat separation with IDEAL gradient-echo imaging*. J Magn Reson Imaging 25(3):644-652 (Mar. 2007).

Schweser, et al., *Quantitative imaging of intrinsic magnetic tissue properties using MRI signal phase: an approach to in vivo brain iron metabolism?* NeuroImage 54(4):2789-2807 (Feb. 2011).

Wang, et at, *Artery and vein separation using susceptibility-dependent phase in contrast-enhanced MRA*. J Magn Reson Imaging 12(5):661-670 (Nov. 2000).

Ghiglia, and Pritt, *Two-dimensional phase unwrapping: theory, algorithms, and software*. Wiley, New York (1998), pp. 188-194.

Jackson, J.D., *Classical Electrodynamics*, 3rd ed. Wiley, New York (1999), pp. 35-40.

\* cited by examiner

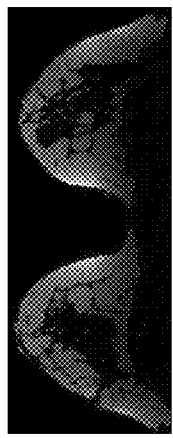
FIG. 4I
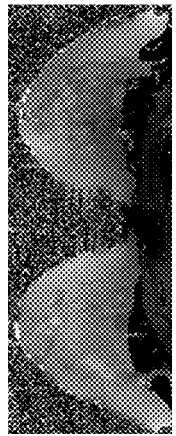
FIG. 4L
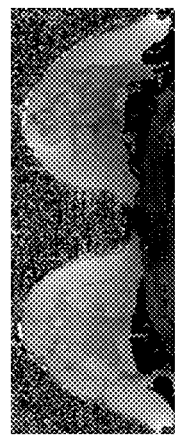
FIG. 4H
FIG. 4K
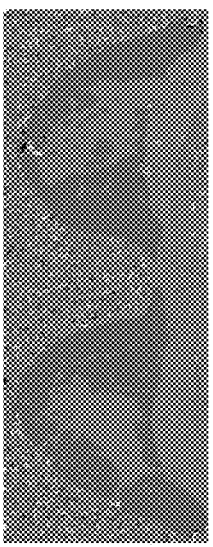
FIG. 4M
FIG. 4G
FIG. 4J

JOINT ESTIMATION OF CHEMICAL SHIFT AND QUANTITATIVE SUSCEPTIBILITY MAP USING MRI SIGNAL

CROSS-REFERENCE TO RELATED APPLICATION

This application claims priority of U.S. Provisional Application Ser. No. 61/839,625, filed Jun. 26, 2013. The content of the prior application is incorporated herein by reference in its entirety.

STATEMENT REGARDING FEDERALLY SPONSORED RESEARCH AND DEVELOPMENT

"This invention was made with government support under Grant No. R43EB015293-01A1 awarded by the National Institutes of Health. The government has certain rights in this invention." This statement is included solely to comply with 37 C.P.R. §401.14(f)(4) and should not be taken as an assertion or admission that the application discloses and/or claims only one invention.

TECHNICAL FIELD

This disclosure relates to magnetic resonance imaging, and more particular to quantitatively mapping material intrinsic physical properties using signals collected in magnetic resonance imaging.

BACKGROUND

Quantitatively mapping out the magnetic susceptibility distribution, also known as quantitative susceptibility mapping (QSM), has received increasing clinical and scientific interest in the community of magnetic resonance imaging (MRI). QSM has shown promising utilities in charactering and quantifying chemical compositions such as iron, calcium, and gadolinium, which are closely related to the diagnosis and treatment of various neurological disorders, such as Parkinson's disease, Alzheimer's disease, stroke, multiple sclerosis, and tumor. It is able to unravel novel information related to the physical property of underlying tissue because the contrast mechanism of QSM is fundamentally different from conventional MRI that is primarily based upon relaxation properties of hydrogen proton. Instead, the contrast in QSM originates from the magnetic moments of the electrons orbiting around the proton. This new kind of contrast mechanism also offers tremendous opportunity to clinicians and engineers to exploit the full utility of MRI scanners at a very low additional cost by studying the phase images generated in a MRI scan.

SUMMARY

The present disclosure describes various implementations of systems and methods for MRI signal collection and processing to reconstruct maps of physical properties intrinsic to a material, for example the magnetic susceptibility map and chemical shift.

One or more of the described implementations overcome limitations in the use of quantitative susceptibility mapping when chemical shift is present. In some cases, a joint estimation of chemical shift and quantitative susceptibility mapping can be performed from a single dataset by discriminating the field inhomogeneities induced by these two sources based on physical principles. For example, chemical shift is a local field shift inside a molecular electron cloud, and susceptibility induces a long range field inhomogeneity outside the electron cloud. The two kinds of field inhomogeneities can be separated through an iterative method to arrive at a sufficiently accurate estimation of chemical shift and susceptibility.

Various aspects of the invention are set forth in the claims.

In general, in an aspect, a method for mapping tissue magnetic susceptibility includes acquiring magnetic resonance (MR) images acquired at multiple echo times, where the MR images correspond to a subject comprising at least two species of protons, and where each species has a different chemical shift in its respective resonance frequency. The method also includes determining, for each species, an estimated chemical shift value. The method also includes determining an estimated map of magnetic field inhomogeneity based on the estimated chemical shift values. The method further includes determining an estimated susceptibility distribution of the subject and an error of each estimated chemical shift value based on the estimated map of magnetic field inhomogeneity and prior information regarding the subject. The method also includes generating an image of the subject based on the estimated susceptibility distribution.

In general, in another aspect, a method for mapping tissue magnetic susceptibility includes acquiring MR images acquired at multiple echo times, where the MR images correspond to a subject comprising at least two species of protons, and where each species has a different chemical shift in its respective resonance frequency. The method also includes determining, for each species, an chemical shift value. The method also includes determining an estimated map of magnetic field inhomogeneity based on the chemical shift values. The method further includes determining an estimated susceptibility distribution of the subject and an error of each chemical shift value based on the estimated map of magnetic field inhomogeneity and prior information regarding the subject. The method also includes generating an image of the subject based on the estimated susceptibility distribution.

In general, in another aspect, a non-transitory computer storage medium is encoded with a computer program, the program including instructions that when executed by data processing apparatus cause the data processing apparatus to perform operations including receiving a user input to present a visual representation of a first prior state of a file system. The operations also include acquiring magnetic resonance (MR) images acquired at multiple echo times, where the MR images correspond to a subject comprising at least two species of protons, and where each species has a different chemical shift in its respective resonance frequency. The operations also include determining, for each species, an estimated chemical shift value. The operations also include determining an estimated map of magnetic field inhomogeneity based on the estimated chemical shift values. The operations also include determining an estimated susceptibility distribution of the subject and an error of each estimated chemical shift value based on the estimated map of magnetic field inhomogeneity and prior information regarding the subject. The operations also include generating an image of the subject based on the estimated susceptibility distribution.

Implementations of these aspect may include one or more of the following features:

In some implementations, the method further includes determining that the errors of each estimated chemical shift value (or chemical shift value) exceed a threshold value, and in response: updating the estimated chemical shift values (or chemical shift values), determining an updated estimated map of magnetic field inhomogeneity based on the updated estimated chemical shift values (or chemical shift values), determining an updated estimated susceptibility distribution of the subject and an updated error of each estimated chemical shift value (or chemical shift value) based on the updated estimated map of magnetic field inhomogeneity and prior information regarding the subject, and generating an updated image of the subject based on the updated estimated susceptibility distribution. In some cases, the method further includes repeating, until the updated error of each estimated chemical shift value (or chemical shift value) does not exceed the threshold, the following steps: updating the estimated chemical shift values (or chemical shift values), determining an updated estimated map of magnetic field inhomogeneity based on the updated estimated chemical shift values (or chemical shift values), determining an updated estimated susceptibility distribution of the subject and an updated error of each estimated chemical shift value (or chemical shift value) based on the updated estimated map of magnetic field inhomogeneity and prior information regarding the subject, and generating an updated image of the subject based on the updated estimated susceptibility distribution.

In some implementations, prior information regarding the subject includes anatomical information regarding the subject. Anatomical information can include an anatomical image of the subject. The estimated susceptibility distribution can be similar to the anatomical image. Anatomical information can include information corresponding to a spatial distribution of each species within the subject. Prior information can include a penalty for abrupt changes in susceptibility between neighboring voxels of the estimated susceptibility distribution.

In some implementations, the subject can be a breast of a patient, a liver of a patient, or a joint of a patient.

In some implementations, acquiring MR images can include acquiring MR images using a gradient echo pulse sequence or an asymmetric spin echo pulse sequence.

In some implementations, one species can correspond to water, and another species can correspond to fat.

In some implementations, the estimated chemical shift value (or chemical shift value) for the species corresponding to fat can be in a range from approximately −3.5 ppm to −3.4 ppm, and the estimated chemical shift value for the species corresponding to water can be about 0 ppm.

In some implementations, the method can further include determining reconstructed images corresponding to each of the species, where the reconstructed images are determined based on an iterative decomposition process, and spatially segmenting each reconstructed image into two or more distinct regions, where each distinct region corresponds to a different species. Segmenting each reconstructed image can include segmenting each reconstructed images according to a threshold value.

In some implementations, determining an estimated susceptibility distribution of the subject can include determining an estimated susceptibility distribution of the subject on a per-voxel basis.

In some implementations, the estimated chemical shift values (or chemical shift values) are determined based on prior information regarding the chemical shift value of each species.

In some implementations, the estimated chemical shift values (or chemical shift values) are determined empirically.

DESCRIPTION OF THE DRAWINGS

FIGS. 4G-I show in axial view an exemplary water map, frequency map, and fat map, respectively, after initial water fat separation with the presumed chemical shift.

FIG. 4J-K show in axial view an exemplary water and fat mask derived from the water and fat map, respectively.

FIG. 4L shows in axial view an exemplary final frequency map.

FIG. 4M shows in axial view an exemplary difference between the final frequency map shown in FIG. 4L and the initial frequency map shown in FIG. 4H.

DETAILED DESCRIPTION

Figure 1:
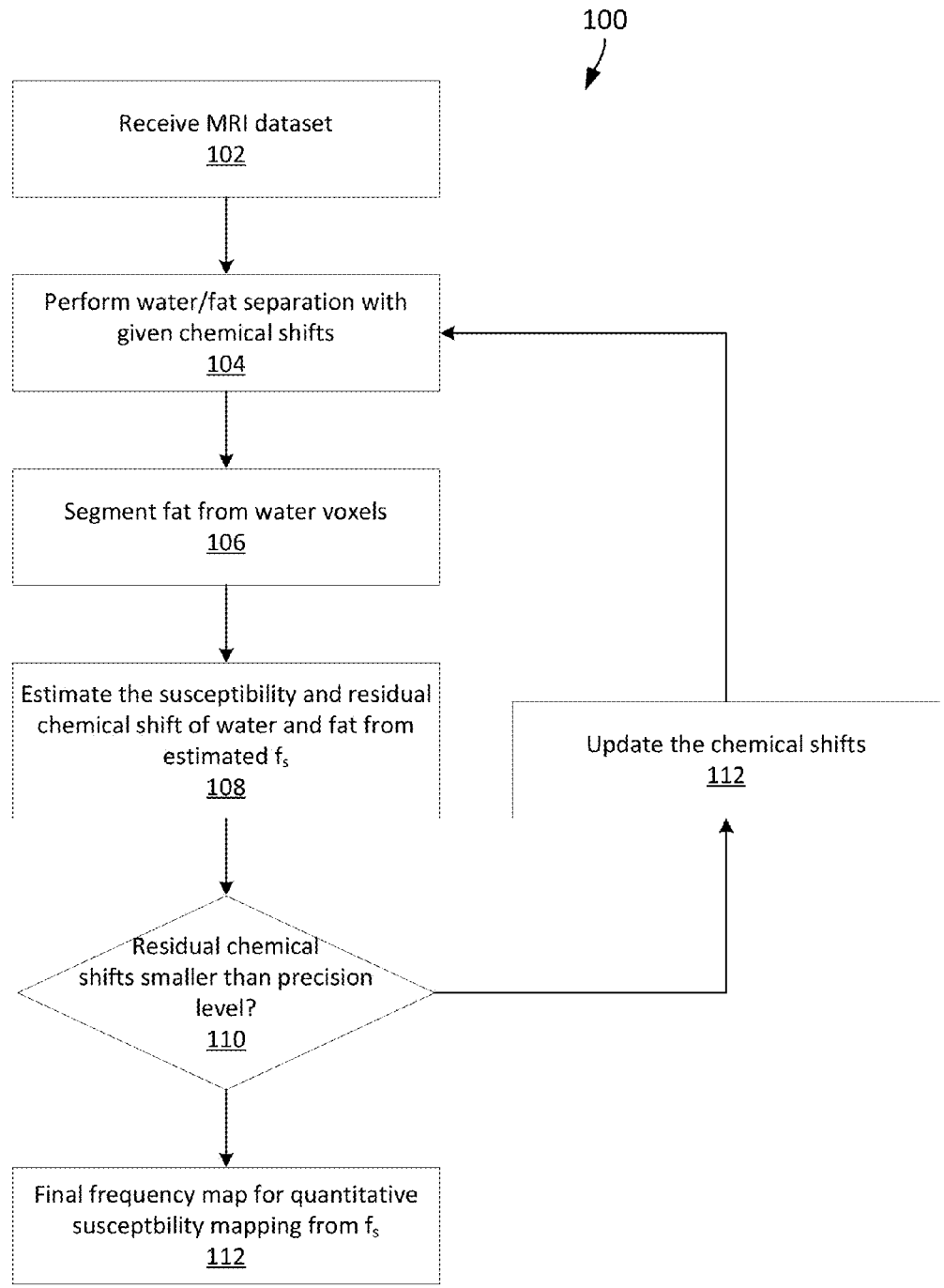
FIG. 1 shows a flow chart of an example iterative process that takes complex MRI data, performs iterative refinement on the chemical shifts, and outputs a frequency map exclusively induced by susceptibility.

It is to be understood that the figures and descriptions of the present invention have been simplified to illustrate elements that are relevant for a clear understanding of the disclosure, while eliminating, for purposes of clarity, other elements that may be well known. The detailed description will be provided herein below with reference to the attached drawings.

A spatially varying magnetic susceptibility distribution (simplified as susceptibility hereafter), when placed in an external magnetic field, can induce its own field. In MRI, the applied field, customarily denoted as $B_0$, is designed to be homogeneous. The induced field is referred as the field inhomogeneity, and affects the measured complex MR image signal, particularly the signal phase. By fitting the phases of a series of measured signals, the field inhomogeneity can be estimated. Further calculation of susceptibility from the estimated field inhomogeneity involves solving a linear $f=D\chi$ or nonlinear $\exp(if)=\exp(-iD\chi)$ system of equations, where f is the estimated magnetic field inhomogeneity, D is a matrix representing the dipole convolution kernel, $\chi$ is the unknown susceptibility, exp is the exponential function, and $i^2=-1$. Although this was considered to be an ill-posed problem lacking a unique solution, advanced mathematical methods incorporating regularization and proper noise characterization have overcome the daunting technical hurdles.

Many of the proposed methods so far assume that susceptibility is the only contributor to the field inhomogeneity, which may be a valid assumption for applications in neuroimaging. However, this prevents the calculation of QSM in situations where other factors also affect the field inhomogeneity, such as the chemical shift of fat. Indeed, the same orbiting electron cloud response to $B_0$ in the molecules that induces a local field inhomogeneity in the surrounding outside the molecule also magnetically shield the nuclei inside the orbiting electron cloud. The shielded protons in the molecule have a resonance frequency different than the unshielded ones, and this resonance frequency offset is referred to as chemical shift.

This chemical shift also affects the complex MRI signal, particularly the signal phase, because the shielded protons contribute to signal generation as well. Although estimation of the field inhomogeneity in the presence of chemical shift has been proposed in various algorithms, these algorithms often assume that the chemical shifts are known a priori. As the chemical shift value may vary from with persons and organs within the same person, the assumed value may not be accurate enough for the subsequent determination of susceptibility. To obtain an accurate measurement of the chemical shift, additional NMR spectroscopy may be required, which may be inconvenient or sometimes impossible to perform. In general, estimation of a quantitative susceptibility map in the presence of chemical shift is still an unsolved problem. A successful solution of to this problem will directly enable applications of QSM in organs containing fat including the heart, liver, kidney, breast, and musculoskeletal system, which are all of clinical interests, especially for the quantification of contrast agents, iron deposition, and calcification.

To illustrate the joint estimation of chemical shift and susceptibility, we first will present an analysis of the MRI signal when the field inhomogeneity includes contributions from both chemical shift and susceptibility, and describe how these inhomogeneities can lead to various challenges in interpreting the MRI signal. We will then introduce an iterative technique to solve the problem of joint estimation of chemical shift and susceptibility, and will describe various exemplary implementations for the technique, along with experimental results demonstrating its practicality.

MRI Signal Model with Chemical Shift and Susceptibility Induced Field Inhomogeneity Field inhomogeneity may be sensitized using various MRI signal acquisition techniques including the gradient echo technique and the asymmetric spin echo technique. As an example, we illustrate the gradient echo acquisition technique. In this example, the reconstructed image signal s of a voxel centered at a spatial location r measured at the nth echo time $TE_n$ may be expressed as:

$$s(r, TE_n) = \exp(-if_s TE_n) \sum_{k=0}^{m-1} \rho_k(r) \exp(if_k TE_n) \exp(-R2_k^*(r) TE_n). \quad [\text{Eq. 1a}]$$

Here, we decompose the total field inhomogeneity f into a spatially varying $f_s(r)$ that is induced by susceptibility, and a constant chemical shift $f_k$ of the kth species. The total number of species in the voxel is m, and their complex signal amplitude at location r immediately after excitation is denoted as $\rho_k(r)$. After excitation, the signal experiences dephasing due to chemical shift and decay characterized by $R2_k^*(r)$. For simplicity, the spatial index (r) may be dropped hereafter whenever clarity is not affected. Each species is characterized by three parameters: $\rho_k$, $f_k$, and $R2_k^*$. The parameters of different species may be independent, such as water and fat, or correlated, such as different components of fat. Without loss of generality and for the sake of clarity, we explicitly expand the summation for a common scenario that only water with $\rho_0$, $f_0$, and $R2_0^*$ and fat with $\rho_1$, $f_1$, and $R2_1^*$ are present, so the Eq. 1a is expanded as:

$$s(r, TE_A) = \exp(-if_s TE_n)[\rho_0 \exp(-R2_0^* TE_n) + \rho_1 \exp(-if_1 TE_n) \exp(-R2_1^* TE_n)] \quad [\text{Eq. 1b}]$$

The chemical shift of water is zero as the water resonance frequency is used as the frequency reference; deviation from 0 would be absorbed by $f_s$. In some cases, this can be customary, but not required. In some cases, it may be useful to further simplify Eq. 1b for situations that both water and fat have the same $2^*$. The simplest form is from $R2^*=0$, $$s(r, TE_n) = \exp(if_s TE_n)[\rho_0 + \rho_1 \exp(-if_1 TE_n)] \quad [\text{Eq. 1c}]$$

To describe the concepts of the disclosure for easy understanding, we illustrate in the following the solution of $f_1$ and $f_s$, in Eq. 1c. The results can be straightforwardly generalized to Eqs. 1b&a by adding $R2_k^*$ and more species.

Challenges in Estimating $f_s$.

In some cases, in may be possible to estimate $f_s$, $\{\rho_k\}_{k=1, 2, \ldots, m}$ by assuming $f_k$ is known a priori, followed by minimizing a cost function defined by the residual between fitted parameters and measured signals over N different TEs:

$$f_s^*, \{\rho_k\}_{k=0,1^*} = \mathrm{argmin}_{f_s, \{\rho_k\}k=0,1} \sum_{n=1}^{N} \quad [\text{Eq. 2}]$$

$$\|s(r, TE_n) - \exp(-if_s TE_n)[\rho_0 + \rho_1 \exp(-if_1 TE_n)]\|^2$$

When only water and fat are present, $f_1$ is often assumed to be between $-3.5$ and $-3.4$ parts per million (ppm). The uncertainty (0.1 ppm) in fat chemical shift (sometimes called off resonance frequency) may not substantially affect the estimation of $\{\rho_k\}_{k=0,1}^*$. However, it has substantial effect in the estimation of $f_s^*$, the inhomogeneity field map (sometimes referred to as a "frequency map" in literature). This can be best understood by examining the signal behavior in a voxel consisting of fat only, where Eq.2 reduces to the following, $$f_s^* = \mathrm{argmin}_{f_s}, \sum_{n=1}^{N} \|s(r, TE_n) - \exp[-i(f_s + f_1) TE_n]\rho_1\|^2.$$

Here, any error $\Delta f_1$ in the presumed chemical shift $f_1$ is translated to the estimate $f_s^*$, because the cost function only relies on the summation of $f_s$ and $f_1$. As the susceptibility under investigation is often on the order of 0.01 ppm~0.1 ppm, a 0.1 ppm error in the field map is very large and, in some cases, prohibits meaningful measurement of susceptibility. Therefore, it is sometimes desirable to treat $f_1$ as an additional unknown that needs to be corrected.

Joint Estimation of Chemical Shift $f_1$ and Susceptibility Map $\chi$

In this example, $f_k$ are also treated as unknowns. Therefore, the search dimension in Eq. 2 needs to be expanded to include $f_k$, which is formulated as the minimization of an energy function defined by summing the residual cost over space occupied by the species:

$$f_s, \{\rho_k, f_k\}_{k=0,1}^* = \mathrm{argmin}_{f_s, \{\rho_k, f_k\}_{k=0,1}} \sum_r \sum_{n=1}^N \quad [\text{Eq. 3}]$$
$$\|s(r, TE_n) - \exp(-if_s TE_n)[\rho_0 + \rho_1 \exp(-if_1 TE_n)]\|^2$$

This is a high dimensional estimation problem and also highly nonlinear. One approach to solve this problem is to decouple $f_s$ and $f_k$ using a fixed-point or inexact newton method while enforcing self-consistency. In short, we aim to find an accurate $f_1$, such that the resulting $f_s$ is consistent with a field explainable by susceptibility distribution. Susceptibility distribution generates a field inhomogeneity according to the dipole convolution $f_s = D\chi$. When non-dipole fields exist in $f_s$, the inverted susceptibility tends to have streaking artifacts. The typical streaking artifacts have spurious edges that do not correspond to any anatomical features known from anatomic MRI including the magnitude image, T1 & T2 weighted images. The anatomic features can be represented in various mathematical forms, such as edges. The correct $f_s$ would have minimal artifact features not present in the known features. One mathematical formulation of this insight is:

$$f_1^*, \chi^* = \mathrm{argmin}_{f_1} |MG_\chi|, \quad [\text{Eq. 4}]$$
$$\text{s.t.} \sum_r \sum_{n=1}^N \left\| \frac{s(r, TE_n) -}{\exp(-iD_\chi TE_n)[\rho_0 + \rho_1 \exp(-if_1 TE_n)]} \right\|^2 = \varepsilon$$

where G is the gradient operator for signifying edges, M is an edge mask derived from the gradient of anatomical prior such as from the magnitude image of the same MRI dataset, ▲ is an estimated noise level. Note that $\{\rho_k\}$ could be treated as dependent variables, since their optimal values are easily determinable in a linear least squares fitting problem using Moore-Penrose pseudoinverse once $f_1^*$, *, or $f_s^*$ are known.

Eq.4 remains to be a very formidable problem, as the nonlinear cost function may contain many local minima that can erroneously trap a search outcome. Implementations of the disclosed technique overcome this false local minima trap by designing a robust research path guided by dominant features of chemical shifts and background field. The chemical shift between water and fat (~3.5 ppm) is very large, causing phase discontinuity, so we can estimate the chemical shift distribution by identifying field discontinuity around 3.5 ppm jump. The background field is harmonic, so we can remove it to zoom onto the field generated by susceptibility. An implementation of this dominant feature first subtle feature second (DFSS) approach to solving nonlinear optimization problem in Eq.3 or Eq.4 is exemplified in the following steps:

Example Iterative Processes for Estimating a Frequency Map

To solve this highly nonlinear problem, an iterative process 100 is devised that takes complex MRI data, performs iterative refinement on the chemical shifts, and outputs a frequency map exclusively induced by susceptibility. A flowchart of an example implementation of the process 100 is shown in FIG. 1. In this process 100, chemical shifts are first iteratively refined based on a regularized estimation of $\chi$. When the desired precision of chemical shifts achieved, the estimated field inhomogeneity will not contain any contribution (or substantially no contribution) from chemical shift, and allows a faithful estimation of $\chi$. An example of detailed steps of the iterative process 100 is described below:

The process 100 starts by receiving an MRI dataset (step 102). In some implementations, the MRI dataset can include one or more gradient echo or asymmetric spin echo MR datasets acquired using varying TE (step 102). For instance, in an example implementation, a multi-echo spoiled gradient echo sequence was performed on a 3 Tesla MRI scanner with the following imaging parameters: echo time (TE)=3.3 ms, echo spacing ΔTE=3.3 ms, number of echoes=8, repetition time=35 ms, flip angle=20°, bandwidth=±62.5 kHz, and voxel size=1×1×1 mm³. Although an example sequence and example parameters are described above, these are merely illustrative. Other sequences and parameters can be used, depending on the implementation.

Next, water/fat separation with given known chemical shifts is performed (step 104). Step 104 can be performed using one or more of the techniques described above (e.g., according to Eq. 2). In some implementations, various values for the chemical shift can be used as an initial guess. For example, in some cases, −3.4 ppm could be used as the initial guess of the chemical shift for fat for simultaneous estimation of $f_s$ and $\{\rho_k\}_{k=0,1}$.

In practice, the cost function in Eq. 2 can be minimized independently for each of the voxels using either a gradient descent based technique, or an exhaustive search over a set of discrete values of $f_s$. A challenge complicating reliable water/fat separation is the water/fat swap problem, namely, that the species is sometimes incorrectly assigned when only a single species is in a voxel and the susceptibility induced inhomogeneity is on the same order of chemical shift. To circumvent this problem, spatial smoothness can be generally imposed on the field map, either by explicitly smoothing the independently estimated field map, or by penalizing the roughness of the field map using regularization. Alternatively, this problem is also avoidable in gradient descent based methods if the initial guess of $f_s$ is close to the truth. This approach does not assume smoothness and keeps full fidelity to the estimated field map. Along this line, a robust calculation of the initial guess of $f_s$ (process 200) will be presented in the next section.

Next, a simple threshold is performed on the fat fraction map (step 106). In some implementations, this threshold can be defined as $K = |\rho_1|/(|\rho_0| + |\rho_1|)$, or $\kappa = |\rho_1|/(|\rho_0| + \rho_1|)$. If $\kappa$ is greater than a certain threshold, then the voxel can be considered as a fat voxel; otherwise it can be considered a water voxel. In some implementations, the threshold value $\kappa$ can be empirically determined. For example, the threshold value $\kappa$ can be approximately 0.4 to 0.8 in some cases. The segmented water and fat masks are denoted as $g_0$ and $g_1$, respectively. The edges of the estimated mask may be viewed as a stringent anatomical prior M.

Next, the susceptibility and residual chemical shift of water and fat is estimated (step 108). Step 108 can be performed using one or more of the techniques described above (e.g., according to Eq. 4). For instance, the estimated $f_s$ from step 104 can be used to update the chemical shifts by solving Eq. 4. In an example implementation, a close form solution to Eq. 4 is achievable under a piece-wise constant model by using the stringent anatomical constraint from step 13, where inside the water or the fat mask, susceptibility and chemical shifts are assumed to be constants. The field map is then a sum of weighted geometric shapes representing water and fat and their dipole convolutions. Using this model, $|MG\chi|$ is guaranteed to be zero, which is the theoretic lower bound. To fulfill the data fidelity constraint in Eq. 4, the local field $f_L$ estimated from $f_s$ at the current iteration is used for calculating the susceptibility $\chi$ and residual chemical shift $\sigma$ of water and fat:

$$\{\chi_k, \sigma_k\}_{k=0,1^*} = \operatorname{argmin}_{\{\chi_k, \sigma_k\}k=0,1} \sum_r \left\| f_L - \sum_{k=0}^{1} \{\chi_k D g_k + \sigma_k g_k\} \right\|^2 \quad [\text{Eq. 5}]$$

The local field $f_L$ could be estimated using the fact that the background field part of the total field is harmonic, e.g., its Laplacian is zero inside a given region of interest (ROI). The local field $f_L$ is defined as the field inhomogeneity generated by magnetizations and chemical shifts in the ROI, e.g., its Laplacian equals to $\mu_0(\frac{1}{3}\nabla - \partial_z^2)m + \nabla^2 \Sigma_k \sigma_k g_k$, with m being the tissue magnetization. One technique of estimating $f_L$ is to find a background dipole distribution that can best explain the field observed in the ROI, and subtract it to obtain the local field. This technique is often termed as Projection onto Dipole Fields (PDF). Another technique of estimating $f_L$ is to utilize the harmonic property of the background field inside the ROI, and remove it using the spherical mean value operation, and this method is often termed as Sophisticated Harmonic Artifact Reduction on Phase (SHARP). In some cases, it is ideal if $f_L$ only reflects local susceptibility contributions, as the chemical contribution should have been removed in the water/fat separation stage (e.g., step 104). Therefore, any difference in residual chemical shifts $\{\sigma_k\}$ indicates an error on the presumed chemical shifts.

In another example implementation, Eq. 4 can be solved with susceptibility estimated on a per voxel basis:

$$\begin{bmatrix} \chi \\ \sigma_0 \\ \sigma_1 \end{bmatrix}* = \operatorname{argmin}_{[\chi^T \sigma_0 \sigma_1]^T} |MG_\chi|, \quad [\text{Eq. 6a}]$$

$$\text{s.t.} \sum_r \left\| W\left( f_L - \begin{bmatrix} D & g_0 & g_1 \end{bmatrix} \begin{bmatrix} \chi \\ \sigma_0 \\ \sigma_1 \end{bmatrix} \right) \right\|^2 = \varepsilon$$

where $\chi$ is a column vector representing spatially varying susceptibility, W is the noise covariance matrix to account for spatially varying noise. The noise propagation may be better compensated using a nonlinear formulation:

$$\begin{bmatrix} \chi \\ \sigma_0 \\ \sigma_1 \end{bmatrix}* = \operatorname{argmin}_{[\chi^T \sigma_0 \sigma_1]^T} |MG_\chi|, \quad [\text{Eq. 6b}]$$

$$\text{s.t.} \sum_r \left\| W\left( \exp(-if_L) - \exp\left(-i\begin{bmatrix} D & g_0 & g_1 \end{bmatrix} \begin{bmatrix} \chi \\ \sigma_0 \\ \sigma_1 \end{bmatrix}\right) \right) \right\|^2 = \varepsilon$$

With simple variable substitution, $\chi' = [\chi^T \sigma_0 \sigma_1]^T$, $G' = [G\ 0\ 0]$, $D' = [D\ g_0\ g_1]$, Eqs. 6a-b are rewritten as:

$$\chi'^* = \operatorname{argmin}_{\chi'} |MG'\chi'|, \quad [\text{Eq. 6c}]$$

$$\text{s.t.} \sum_r \|W(f_L - D'\chi')\|^2 = \varepsilon$$

The constrained minimization problems in Eqs. 6c-d can be reformulated as an unconstrained Lagrangian minimization problem, $$\chi^* = \operatorname{argmin}_\chi L(\chi) + \alpha R(\chi) \quad [\text{Eq. 6d}]$$

with $L(\chi)$ denoting the data fidelity term, either $\Sigma_r \|W(\exp(-if_L) - \exp(-iD\chi))\|^2$ or $\Sigma_r \|W(f_L - D\chi)\|^2$, and $R(\chi)$ denoting the regularization term $|MG\chi|$. The solution to this unconstrained minimization coincides with the one to the constrained minimization problem with a properly chosen regularization parameter $\alpha$. The unconstrained minimization problem can be efficiently solved using nonlinear solvers commonly used for solving L1 norm minimization, such as the inexact Newton technique. In this technique, the function $L(\chi) + \alpha R(\chi)$ is repeatedly updated with a series of candidate solutions resulting in gradually decreasing costs. With proper linearization after each candidate solution, an update is calculated as the inverse of the Hessian of the cost function applied on the gradient of the cost function at that candidate solution. The iteration stops when the update is sufficiently small or the number of iteration exceeds a limit. The estimated $\chi^*$ contains exactly a joint estimation of susceptibility and chemical shifts.

If the difference on residual chemical shifts is larger than a tolerance level, or the estimated susceptibility map is unsatisfactory (step 110), the chemical shifts are updated by adding the residual chemical shifts (step 112), and the process returns to step 104. Otherwise, the process proceeds to step 114 if the piece-wise constant model is used.

The final estimated frequency map $f_s$ is passed to the next stage for quantitative susceptibility mapping (step 114). For example, in some implementations, a final susceptibility map can be calculated based on the estimate frequency map $f_s$. In some cases, this susceptibility map can represent the tissue susceptibility of the subject, and can be used to determine iron concentration, calcification density, and contrast agent concentration.

Figure 2A:
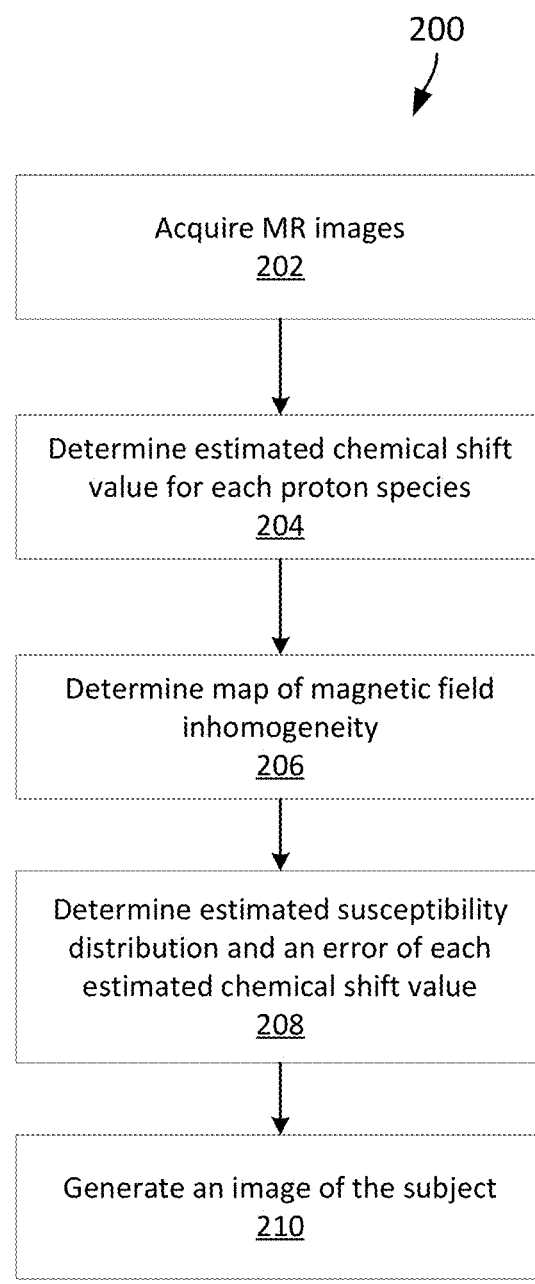
FIG. 2A shows a flow chart of an example process for determining a susceptibility map corresponding to the subject.

Another example process 200 is shown in FIG. 2A. Like process 100, process 200 can use one or more of the techniques described above in order to acquire MR data of a subject (e.g., MR images), determine a frequency map corresponding to the subject, and determine a susceptibility map corresponding to the subject. Implementations of process 200 can be used, for example, to generate an image of the subject based on an estimated susceptibility distribution of the subject.

The process 200 begins by acquiring magnetic resonance (MR) images (step 202). In some implementations, MR images can be acquired at multiple echo times, for example with an MRI scanner using a suitable pulse sequence (e.g., a sequence and set of parameters described above). As an example, a gradient echo pulse sequence or an asymmetric spin echo pulse sequence can be used to acquire MR images.

Depending on the application, the subject of the MR images can include two or more different species of protons. As an example, if the subject is a body part of a patient (e.g., a breast, a liver, a joint, or some other body part of the patient), the subject might be composed of at least two different species of protons. As an example, in some cases, one species of protons might correspond to fat (e.g., distributions of fat within the subject and/or surrounding the subject), while another species of protons might correspond to water (e.g., distributions of water within the subject and/or surrounding the subject). As discussed above, each species of proton might have a different chemical shift in its respective resonance frequency. For example, the species of protons corresponding to fat might have a particular chemical shift in its respective resonance frequency, and the species of protons corresponding to the water might have a different chemical shift in its respective resonance frequency. Although two species are described in these examples, in some cases the subject can include more than two species, and the process 200 can consider more than two species during analysis (e.g., as described above).

After acquiring MR images, the process continues by determining, for each species of protons, an estimated chemical shift value (step 204). As described above, this estimated chemical shift value can be determined based on prior knowledge (e.g., based on previously determined chemical shift values of the corresponding species of protons, such as empirically determined chemical shift values or observed chemical shift values), or using some other method (e.g., based on the process 300 described below). In some cases, this estimated chemical shift value can be considered a "guess" of the unknown actual chemical shift value. As examples, in some cases, the actual chemical shift values for species corresponding to fat and water might not be known, and the estimated chemical shift value for the species corresponding to fat is in a range from approximately −3.5 ppm to −3.4 ppm, while the estimated chemical shift value for the species corresponding to water is about 0 ppm. Other estimated chemical shift values can be used, depending on the application.

After determining estimated chemical shift values, the process continues by determining an estimated map of magnetic field inhomogeneity based on the estimated chemical shift values (step 206). As described above, the map of magnetic field inhomogeneity (i.e., an estimated "frequency map," $f_s^*$) can be determined based on the relationships described above (e.g., as described above with respect to Eq. 2).

After estimating a map of magnetic field inhomogeneity, the process continues by determining an estimated susceptibility distribution of the subject and an error of each estimated chemical shift value (i.e., a "residual chemical shift") (step 208). As described above, this can be determined can be based on the estimated map of magnetic field inhomogeneity and prior information regarding the subject (e.g., as described above with respect to Eq. 4). As discussed above, the prior information regarding the subject can be used to regularize the determination. For instance, in some implementations, prior information regarding the subject might include anatomical information regarding the subject. As an example, anatomical information can include MR images of the subject (e.g., an magnitude MR image), depicting a similar portion of the subject with a similar perspective and field of view). As another example, anatomical information can include prior knowledge about the spatial distribution of each species within the subject (e.g., a spatial map of fat and water in and around the subject). As described above, this prior information can be used to regularize the determination. For example, the susceptibility distribution might be estimated in a manner that favors estimated susceptibility distributions that are at least partially similar to the anatomical image (e.g., such that they at least partially share similar features, intensity distributions, and so forth). As another example, the susceptibility distribution might be estimated in a manner that considers the spatial distribution of each species within the subject. As yet another example, the susceptibility distribution might be estimated in a manner that penalizes abrupt changes in susceptibility between neighboring voxels of the estimated susceptibility distribution. Although examples of prior knowledge are described here, other types of prior knowledge can also be used to regularize the determination.

The process continues by generating an image of the subject based on the estimated susceptibility distribution (step 210). As an example, in some implementations, the estimated susceptibility distribution can be presented as one or more image or volumes, where each pixel or voxel has an intensity value based on a corresponding pixel of voxel of the estimated susceptibility distribution. In this manner, the estimated susceptibility distribution of the subject can be visually assessed (e.g., by a user examining the image), and can be used to provide sources of image contrast that might not be readily available on other images of the subject.

Figure 2B:
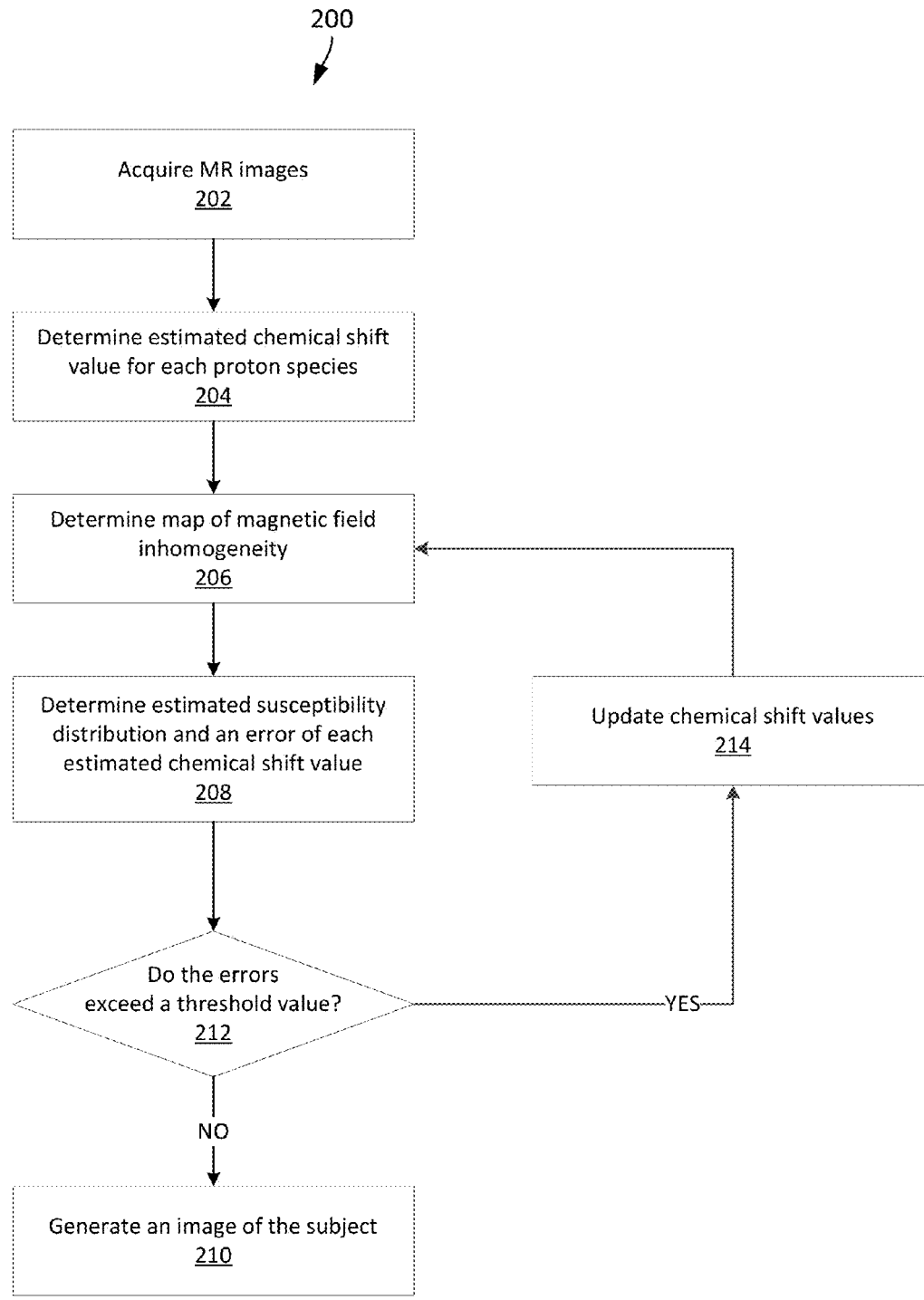
FIG. 2B shows a flow chart of another example process for determining a susceptibility map corresponding to the subject.

As described above, in some implementations, the determination of the map of magnetic field inhomogeneity (i.e., the frequency map) and the corresponding susceptibility distribution can be an iterative process. An example of an iterative process 250 is shown in FIG. 2B. In this example, the process 250 is similar to process 200 shown in FIG. 2A, but repeats certain steps based on the errors of each estimated chemical shift value. For example, as shown in FIG. 2B, steps 202, 204, 206, and 208 proceed as described with respect to FIG. 2A. However, upon determining an estimated susceptibility distribution and error of each estimated chemical shift value, the process can include determining if one or more of the errors exceeds a particular threshold value. As one example, this condition can be met if one error exceeds a particular threshold value. As another example, this condition can be met if multiple error values (e.g., corresponding to some or all of the chemical shift values) exceed a particular threshold value. In some implementations, different threshold values can be used for each error value. For example, a first threshold value might be used with respect to a first error value pertaining to a first chemical shift value, and a second threshold value might be used with respect to a second error value pertaining to a second chemical shift value.

If the condition is met, the estimated chemical shift values are updated with new values (step 214). As described above, the estimated chemical shift values can be updated in a variety of ways. For example, in some implementations, each error can be added to its corresponding estimated chemical shift value in order to obtain an updated chemical shift value.

After the estimated chemical shift values are updated, the process continues back to step 206, and an updated estimated map of magnetic field inhomogeneity, estimated susceptibility distribution, and errors are determined based on the updated chemical shift values. In some implementations, these steps can repeat until the errors no longer exceed the threshold value, such that an acceptable solution is determining after one or more iterations of steps.

Example Process for Determining an Initial Guess of $f_s$

Figure 3:
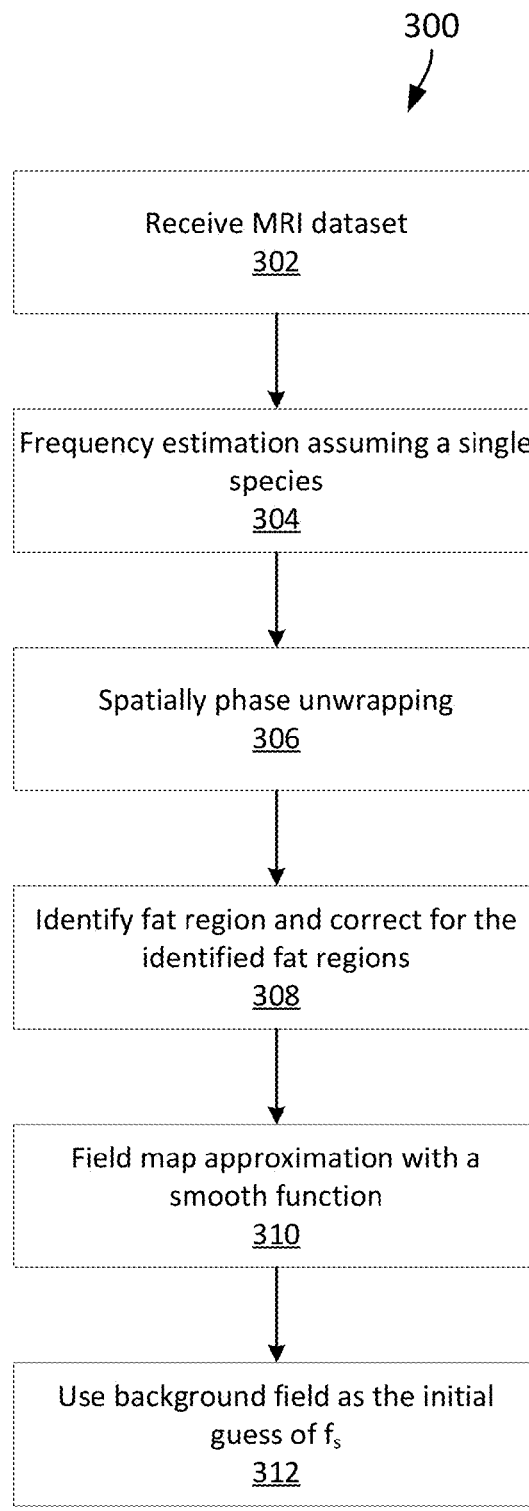
FIG. 3 shows a flow chart of an example process to estimate the initial guess of susceptibility induced field inhomogeneity.

As described above, a robust calculation of the initial guess of $f_s$ can be used in conjunction with the process 100 and process 200. An example implementation of this process 300 is shown in FIG. 3.

The process 300 starts by receiving an MRI data set (step 302). As above, in some implementations, the MRI dataset can include one or more gradient echo or asymmetric spin echo MR datasets acquired using varying TE.

A single species model is assumed in each voxel and the frequency map is fitted assuming a linear phase evolution (step 304). For example, in some cases, in the linear phase evolution model, the phase is assumed to linearly increase with echo time. In this cases, a linear regression of the phase might elucidate the rate at which the phase is changing, where the rate is the off-resonance frequency at that voxel.

Because of the limited dynamic range, which is essentially determined by $1/\Delta TE$ with $\Delta TE$ denoting the TE spacing, frequency aliasing or wrapping appears on the estimated field map. This is addressed by performing a path based phase unwrapping (step 306). In some implementations, the unwrapping path is based on the estimated noise level of the field map and spatial connectivity, so that high quality regions are unwrapped first. In some implementations, phase unwrapping is performed by applying a minimum norm based phase unwrapping method, which essentially minimizes the difference between the Laplacian or gradient of the unwrapped field map and the Laplacian or gradient derived from the original wrapped field map.

Because a single species is assumed, the apparent frequency offset in fat voxels is the summation of chemical shift and susceptibility induced inhomogeneity. The additional chemical shift causes large spatial discontinuities in the frequency map, and allows easy identification of the fat regions (step 308). As an example, fat can be identified by inspecting the difference between two neighboring voxels. If the difference is close to the expected difference caused by chemical shift (e.g., within a particular range of values), it is likely that this is the border of two different species. Once the regions are identified, the chemical shift is corrected using the presumed fat off resonance frequency.

Next, the field map is approximated with a smooth function (step 310). In many applications, the background field is a smooth function and orders of magnitude stronger than the local fields, so the background field is a good approximation of the field inhomogeneity $f_s$. In addition to PDF and SHARP, low pass filtering could be used to estimate the background field, where the background field is assumed to be representable by low frequency Fourier basis of the original image, effectively using a low resolution version of the original image to approximate the background field. There is not a specific requirement on the choice of techniques, as long as the chosen technique provides a smooth background field. The smoothness of the background field teases out outlier points caused by noise or errors in unwrapping.

The smooth background field is served as the initial guess of $f_s$ and passed to water/fat separation (step 312). As an example, the smooth background field can be passed to step 104 of process 100, or to step 206 of process 200 or 250.

EXPERIMENTS

Experiments were performed to evaluate the effectiveness of implementations of the above described iterative refinement technique.

In an example experiment, a female volunteer (36 years old) was recruited for breast MR imaging on a 3T scanner (Siemens, Erlangen, Germany). A unipolar multi-echo gradient echo sequence was used. Other imaging parameters included: TR=35 ms, 8 TEs evenly spaced between 3.28 ms to 26.24 ms, bandwidth=625 Hz/voxel, field of view=32 cm, slice thickness=1 mm, acquisition matrix=320×320×96. An integrated Parallel Acquisition Technique (iPAT) was enabled with an acceleration factor of 2. Magnitude and phase DICOM images were saved for post-processing.

In this experiment, two different reconstruction strategies were employed for comparison. In the first one, the frequency map was estimated from IDEAL using the presumed fat chemical shift −3.5 ppm, followed by the Morphology Enabled Dipole Inversion with Nonlinear data fidelity formulation (MEDI). This reconstruction served as the baseline reconstruction for evaluating any improvement in the second reconstruction. In the second one, the frequency map was estimated using the IDEAL with an iteratively refined fat chemical shift. The iteration stopped when the update was smaller than 1 Hz. QSM was then reconstructed using the same MEDI algorithm. In the j-th refinement iteration, we also recorded the cost of the energy function in Eq. 3 after IDEAL as a function of the updated fat chemical shift $f_f^{(j)}$:

$$cost^{(k)} = \sum_r \sum_{n=1}^{N} \left\| s(r, TE_n) - \exp(-if_s^{(j)}TE_n)[\rho_0^{(j)} + \rho_1^{(j)}\exp(-if_1^{(j)}TE_n)] \right\|^2.$$

Note that energy function in Eq. 3 is what we aim to minimize, and the examination on the cost function will verify our goal.

Figure 4B:
FIG. 4A and FIG. 4B shows in axial view the received magnitude and phase images of the multi-echo gradient echo dataset from exemplary breast MRI, respectively.
Figure 4D:
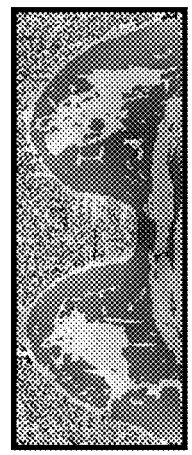
FIG. 4D shows in axial view an exemplary unwrapped frequency map.
Figure 4F:
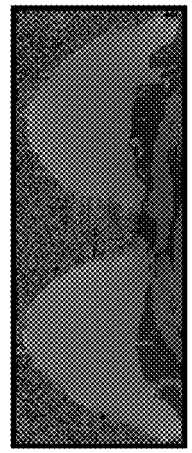
FIG. 4F shows in axial view an exemplary background field estimated from the fat corrected frequency map.
Figure 4A:
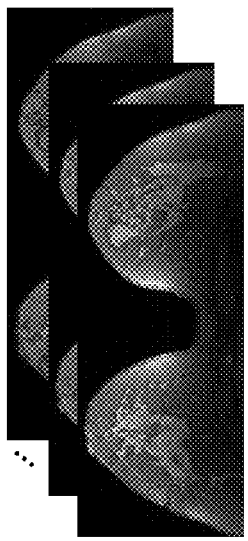
Figure 4C:
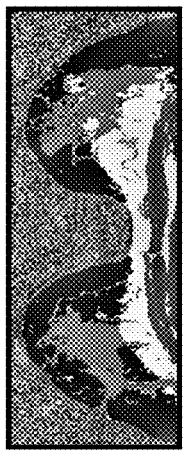
FIG. 4C shows in axial view an exemplary frequency map estimated from linear phase evolution.
Figure 4E:
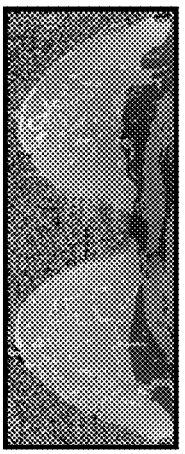
FIG. 4E shows in axial view an exemplary the fat corrected frequency map.

Exemplary intermediate and final results are shown in FIGS. 4A-M and FIGS. 5A-E. After the original complex multi-echo MRI dataset was received (FIGS. 4A-B), the initial guess of $f_s$ was estimated using a linear phase evolution model (FIG. 4C), followed by phase unwrapping (FIG. 4D), fat correction (FIG. 4E), and a field map approximation (FIG. 4F). Water map (FIG. 4G), fat map (FIG. 4I) and frequency map (FIG. 4H) were calculated using IDEAL. The water and fat map also allowed easy segmentation with a threshold $\kappa=0.7$ to generate a water mask (FIG. 4J) and fat mask (FIG. 4K).

Figure 5A:
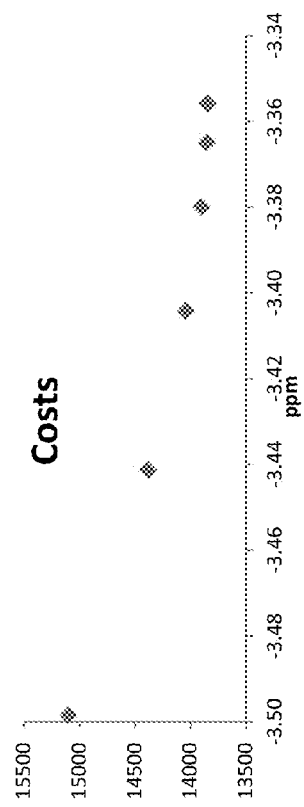
FIG. 5A shows plot depicting the monotonically decreasing costs of the energy function that we aim to minimize.
Figure 5C:
FIG. 5C shows in axial view an example of an improved QSM solution using refined chemical shift.
Figure 5B:
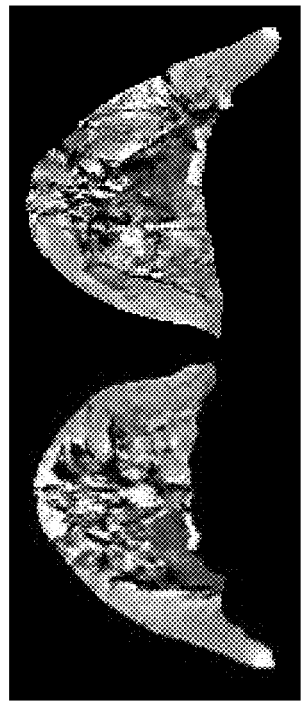
FIG. 5B shows in axial view an exemplary QSM solution of the case shown in FIGS. 4A-M.
Figure 5D:
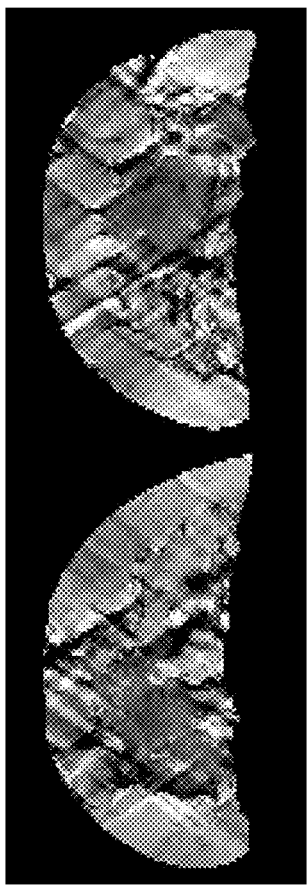
FIG. 5D shows in coronal view an exemplary QSM solution of the case shown in FIGS. 4A-M using presumed chemical shift.
Figure 5E:
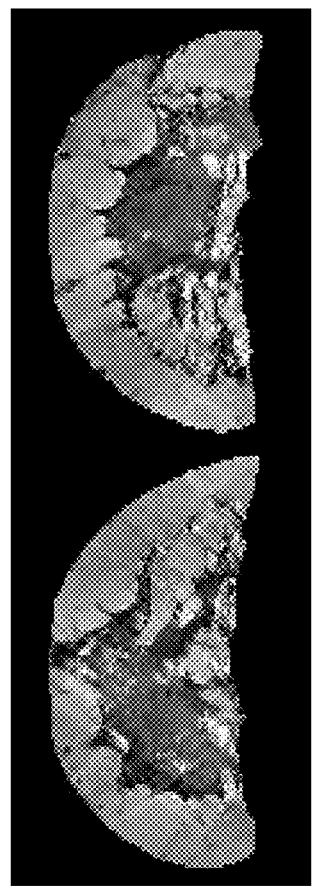
FIG. 5E shows in coronal view an example of an improved QSM solution using refined chemical shift.

In an example implementation, these two masks and the frequency map (FIG. 4H) was used to update the chemical shifts with a piece-wise constant model in the interest of computational speed. After 6 iterations, the fat chemical shift converged to −3.36 ppm from initial −3.5 ppm with monotonically decreasing costs (FIG. 5A). The final frequency map was presented in FIG. 4L, and its difference with the first frequency map after $1^{st}$ IDEAL (FIG. 4H) is shown in FIG. 4M. It is noticed that the fat region has a smaller frequency offset at the final frequency map. The reconstructed QSM from the first frequency map using the presumed chemical shift −3.5 ppm and the QSM from the final frequency map using refined chemical shift −3.36 ppm are shown in FIGS. 5B-C. Artifacts preventing clear depiction of the mammary gland pointed by black arrows are reduced in the latter one. The artifact reduction is more conspicuous by inspecting the coronal plane (black arrows in FIGS. 5D-E). It was shown that fat (solid white arrow) has a higher susceptibility than the water (dashed white arrow) in the glands, and the difference between water and fat in this case ranged between 0.15~0.75 ppm. In another example implementation, a joint estimation of susceptibility and chemical shifts using Eq. 6d was performed and the refinement converged in one iteration. The estimated chemical shift of fat with respect to water was −3.37 ppm, and the calculated susceptibility was identical to the ones presented in FIGS. 5C and 5E upon visual inspection.

APPLICATIONS

Quantitative susceptibility mapping may be particularly useful for dynamic contrast enhanced (DCE) MRI, where the concentration of contrast agents may indicate the malignancy of the tumors. Since susceptibility of contrast agents increases linearly with the concentration, there has been strong interest in applying QSM to image all the body parts beyond the brain. However, the strong interest is hampered by the reality that susceptibility estimation with the presence of chemical shift is a technical problem that has not been solved. The techniques described here is a timely response to this critical problem, and enables QSM to be applied beyond the brain.

Although only an exemplary breast imaging is shown in the disclosure as an illustrative example, the disclosed implementation do not make specific assumptions or requirements about the geometry or signal generation of breast MRI. Thus, the application of the disclosed implementations is not limited to breast imaging, and is readily applicable to imaging heart, liver, kidney, musculoskeletal system, joints such as ankle, knee, and/or shoulder, or essentially any body parts that have both susceptibility and chemical shift induced field inhomogeneity.

Figure 6:
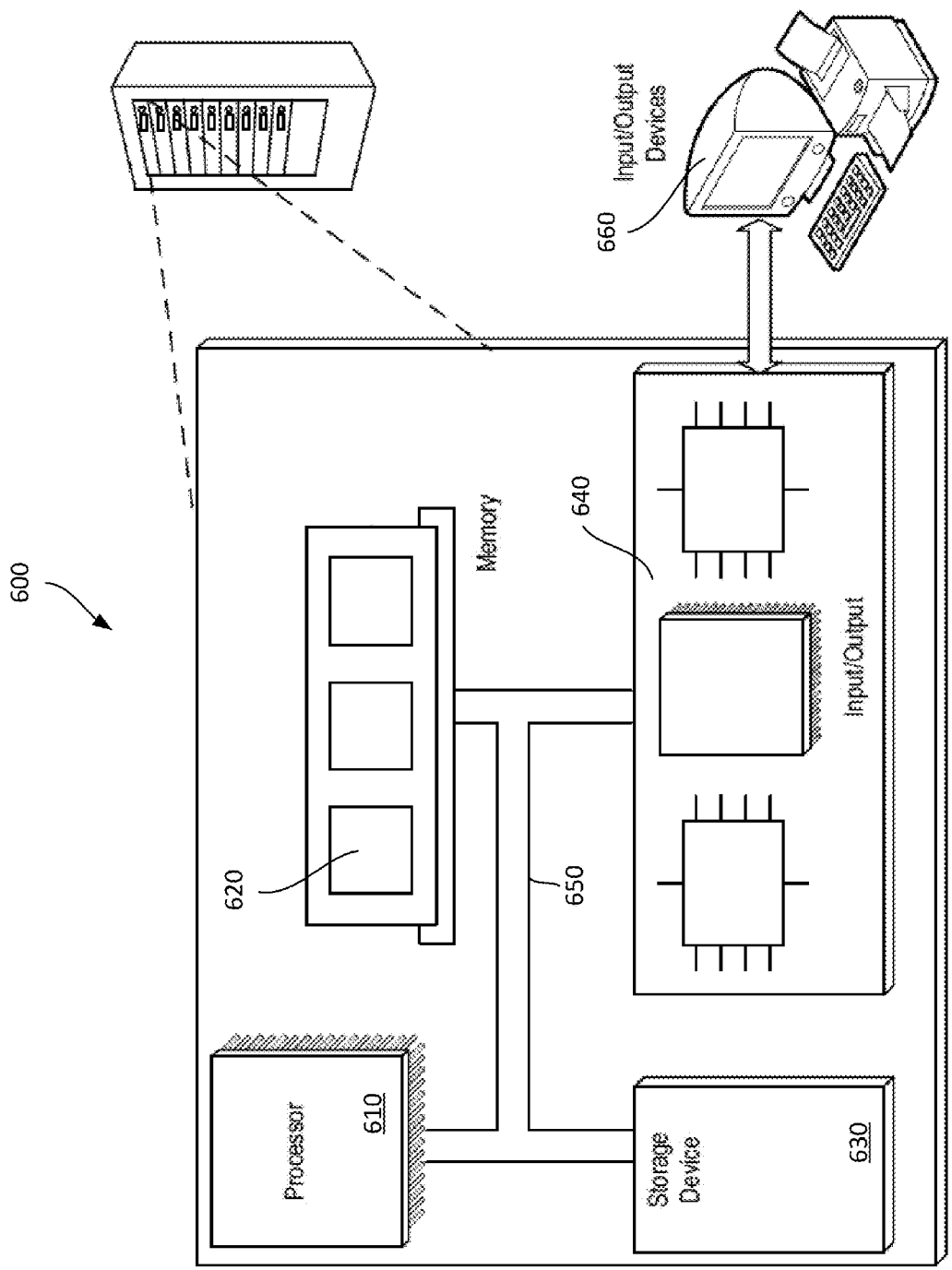
FIG. 6 shows an example computer system.

Implementations of the above described techniques can be performed using a computer system. FIG. 6 is a block diagram of an example computer system 600 that can be used, for example, to perform implementations of the process 100, 200 and/or 300. In some implementations, the computer system 600 can be communicatively connected to another computer system (e.g., another computer system 600), such that it receives data (e.g., MRI datasets), and analyzes the received data using one or more of the techniques described above.

The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. In some implementations, the processor 610 is a single-threaded processor. In some implementations, the processor 610 is a multi-threaded processor. In some implementations, the processor 610 is a quantum computer. The processor 610 is capable of processing instructions stored in the memory 620 or on the storage device 630. The processor 610 may execute operations such as performing one or more of the techniques described above.

The memory 620 stores information within the system 600. In some implementations, the memory 620 is a computer-readable medium. In some implementations, the memory 620 is a volatile memory unit. In some implementations, the memory 620 is a non-volatile memory unit.

The storage device 630 is capable of providing mass storage for the system 600. In some implementations, the storage device 630 is a non-transitory computer-readable medium. In various different implementations, the storage device 630 can include, for example, a hard disk device, an optical disk device, a solid-state drive, a flash drive, magnetic tape, or some other large capacity storage device. In some implementations, the storage device 630 may be a cloud storage device, e.g., a logical storage device including multiple physical storage devices distributed on a network and accessed using a network. In some examples, the storage device may store long-term data. The input/output device 640 provides input/output operations for the system 600. In some implementations, the input/output device 640 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. A network interface device allows the system 600 to communicate, for example, transmit and receive data. In some implementations, the input/output device can include driver devices configured to receive input data and send output data to other input/output devices, e.g., a keyboard, a mouse, a printer, a sensor (e.g., a sensor that measures component or system-related properties, a sensor that measures environmental-related properties, or other types of sensors), and a display device 660. In some implementations, mobile computing devices, mobile communication devices, and other devices can be used.

A computing system can be realized by instructions that upon execution cause one or more processing devices to carry out the processes and functions described above, for example, storing, maintaining, and displaying artifacts. Such instructions can include, for example, interpreted instructions such as script instructions, or executable code, or other instructions stored in a computer readable medium. A computing system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as performing one or more of the above described processes, can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "processing module" may encompass all apparatus, devices, and machines for processing data, including by way of example a programmable processor, a computer, or multiple processors or computers. A processing module can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

Other embodiments are in the following claims.

What is claimed is:

1. A method for mapping tissue magnetic susceptibility, the method comprising:
   acquiring magnetic resonance (MR) images acquired at multiple echo times, wherein the MR images correspond to a subject comprising at least two species of protons, and wherein each species has a different chemical shift in its respective resonance frequency;
   determining, for each species, an estimated chemical shift value;
   determining an estimated map of magnetic field inhomogeneity based on the estimated chemical shift values;
   determining an estimated susceptibility distribution of the subject and an error of each estimated chemical shift value based on the estimated map of magnetic field inhomogeneity and prior information regarding the subject;
   generating an image of the subject based on the estimated susceptibility distribution.

2. The method of claim 1, further comprising:
   determining that the errors of each estimated chemical shift value exceed a threshold value, and in response:
   updating the estimated chemical shift values;
   determining an updated estimated map of magnetic field inhomogeneity based on the updated estimated chemical shift values;
   determining an updated estimated susceptibility distribution of the subject and an updated error of each estimated chemical shift value based on the updated estimated map of magnetic field inhomogeneity and prior information regarding the subject; and
   generating an updated image of the subject based on the updated estimated susceptibility distribution.

3. The method of claim 2, further comprising:
   repeating, until the updated error of each estimated chemical shift value does not exceed the threshold, steps comprising:
   updating the estimated chemical shift values;
   determining an updated estimated map of magnetic field inhomogeneity based on the updated estimated chemical shift values;
   determining an updated estimated susceptibility distribution of the subject and an updated error of each estimated chemical shift value based on the updated estimated map of magnetic field inhomogeneity and prior information regarding the subject; and
   generating an updated image of the subject based on the updated estimated susceptibility distribution.

4. The method of claim 1, wherein prior information regarding the subject comprises anatomical information regarding the subject.

5. The method of claim 4, wherein anatomical information comprises an anatomical image of the subject.

6. The method of claim 5, wherein the estimated susceptibility distribution is similar to the anatomical image.

7. The method of claim 4, where anatomical information comprises information corresponding to a spatial distribution of each species within the subject.

8. The method of claim 4, wherein prior information comprises a penalty for abrupt changes in susceptibility between neighboring voxels of the estimated susceptibility distribution.

9. The method of claim 1, wherein the subject is a breast of a patient.

10. The method of claim 1, wherein the subject is a liver of a patient.

11. The method of claim 1, wherein the subject is a joint of a patient.

12. The method of claim 1, acquiring MR images comprises acquiring MR images using a gradient echo pulse sequence or an asymmetric spin echo pulse sequence.

13. The method of claim 1, wherein one species corresponds to water, and wherein another species corresponds to fat.

14. The method of claim 1, wherein the estimated chemical shift value for the species corresponding to fat is in a range from approximately −3.5 ppm to −3.4 ppm, and wherein the estimated chemical shift value for the species corresponding to water is about 0 ppm.

15. The method of claim 1, further comprising:
   determining reconstructed images corresponding to each of the species, wherein the reconstructed images are determined based on an iterative decomposition process; and
   spatially segmenting each reconstructed image into two or more distinct regions, wherein each distinct region corresponds to a different species.

16. The method of claim 15, wherein segmenting each reconstructed image comprises segmenting each reconstructed images according to a threshold value.

17. The method of claim 1, wherein determining an estimated susceptibility distribution of the subject comprises determining an estimated susceptibility distribution of the subject on a per-voxel basis.

18. The method of claim 1, wherein the estimated chemical shift values are determined based on prior information regarding the chemical shift value of each species.

19. The method of claim 1, wherein the estimated chemical shift values are determined empirically.

20. A non-transitory computer storage medium encoded with a computer program, the program comprising instructions that when executed by data processing apparatus cause the data processing apparatus to perform operations comprising:

receiving a user input to present a visual representation of a first prior state of a file system;

acquiring magnetic resonance (MR) images acquired at multiple echo times, wherein the MR images correspond to a subject comprising at least two species of protons, and wherein each species has a different chemical shift in its respective resonance frequency;

determining, for each species, an estimated chemical shift value;

determining an estimated map of magnetic field inhomogeneity based on the estimated chemical shift values;

determining an estimated susceptibility distribution of the subject and an error of each estimated chemical shift value based on the estimated map of magnetic field inhomogeneity and prior information regarding the subject;

generating an image of the subject based on the estimated susceptibility distribution.

* * * * *